United States Patent
Yamada (10) Patent No.: US 10,182,963 B2
(45) Date of Patent: Jan. 22, 2019

(54) VIBRATION GENERATING UNIT, VIBRATING BODY UNIT AND ULTRASONIC TREATMENT INSTRUMENT

(71) Applicant: OLYMPUS CORPORATION, Hachioji-shi, Tokyo (JP)

(72) Inventor: Masashi Yamada, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/288,576

(22) Filed: Oct. 7, 2016

(65) Prior Publication Data

US 2017/0020777 A1    Jan. 26, 2017

Related U.S. Application Data

(63) Continuation of application No. PCT/JP2015/069762, filed on Jul. 9, 2015.

(30) Foreign Application Priority Data

Sep. 22, 2014  (JP) .................. 2014-192984

(51) Int. Cl.
*B06B 1/06*  (2006.01)
*A61B 17/32* (2006.01)
*A61H 23/02* (2006.01)

(52) U.S. Cl.
CPC ..... *A61H 23/02* (2013.01); *A61B 17/320068* (2013.01); *A61H 23/0245* (2013.01); *B06B 1/0644* (2013.01); *A61B 17/320092* (2013.01)

(58) Field of Classification Search
None
See application file for complete search history.

(56) References Cited

U.S. PATENT DOCUMENTS

2001/0020808 A1   9/2001  Suzuki et al.
2002/0044171 A1*  4/2002  Hirahara ............. B41J 2/14008
                                                     347/46

(Continued)

FOREIGN PATENT DOCUMENTS

CN       1117436 A    2/1996
CN     101765495 A    6/2010

(Continued)

OTHER PUBLICATIONS

Zhou et al., "Technique for Reducing Variance in Transducer Array Pulse-Echo Response," Aug. 23, 2004, IEEE International Ultrasonics, Ferroelectrics, and Frequency Control Joint 50th Anniversary Conference, pp. 2211-2214.*

(Continued)

*Primary Examiner* — Patricia J Park
*Assistant Examiner* — Nate Sunwoo
(74) *Attorney, Agent, or Firm* — Oliff PLC (57) ABSTRACT

A vibration generating unit includes an element unit, and the element unit includes a piezoelectric element generating an ultrasonic vibration by being supplied with electric power. A proximal-side fixing member abuts on the element unit from a proximal direction side and a distal-side fixing member abuts on the element unit from a distal direction side such that the element unit is sandwiched between the proximal-side fixing member and the distal-side fixing member in a longitudinal direction. The distal-side fixing member has a greater acoustic impedance than the proximal-side fixing member.

13 Claims, 7 Drawing Sheets

(56) References Cited

U.S. PATENT DOCUMENTS

| | | | | |
|---|---|---|---|---|
| 2009/0030311 A1* | 1/2009 | Stulen | ............ | A61B 17/320092 |
| | | | | 600/439 |
| 2013/0066238 A1 | 3/2013 | Irisawa et al. | | |
| 2013/0090576 A1* | 4/2013 | Stulen | ............ | A61B 17/320092 |
| | | | | 601/2 |
| 2013/0274637 A1 | 10/2013 | Akagane | | |
| 2014/0336646 A1 | 11/2014 | Irisawa et al. | | |
| 2015/0088154 A1* | 3/2015 | Vaitekunas | ............ | A61B 17/12 |
| | | | | 606/128 |

FOREIGN PATENT DOCUMENTS

| | | |
|---|---|---|
| EP | 0 765 637 A2 | 4/1997 |
| EP | 2 095 779 A1 | 9/2009 |
| JP | S53-118392 A | 10/1978 |
| JP | H10-178700 A | 6/1998 |
| JP | 2001-239405 A | 9/2001 |
| JP | 2011/005467 A | 1/2011 |
| JP | 5259883 B2 | 8/2013 |
| WO | 2005/044509 A1 | 5/2005 |

OTHER PUBLICATIONS

Oct. 6, 2015 Search Report issued in International Patent Application No. PCT/JP2015/069762.
Mar. 28, 2017 International Preliminary Report on Patentability issued in International Application No. PCT/JP2015/069762.
Apr. 5, 2018 Search Report issued in European Application No. 15843669.1.
Apr. 11, 2018 Office Action issued in Chinese Application No. 201580022467.9.

\* cited by examiner

VIBRATION GENERATING UNIT, VIBRATING BODY UNIT AND ULTRASONIC TREATMENT INSTRUMENT

CROSS-REFERENCE TO RELATED APPLICATIONS

This is a Continuation Application of PCT Application No. PCT/JP2015/069762, filed Jul. 9, 2015 and based upon and claiming the benefit of priority from prior Japanese Patent Application No. 2014-192984, filed Sep. 22, 2014, the entire contents of which are incorporated herein by reference.

BACKGROUND OF THE INVENTION

1. Field of the Invention

The present invention relates to a vibration generating unit including a piezoelectric element which generates an ultrasonic vibration by being supplied with electric power. The invention also relates to a vibrating body unit including the vibration generating unit, and an ultrasonic treatment instrument including the vibrating body unit.

2. Description of the Related Art

PCT International Publication No. 2011/005467 discloses an ultrasonic treatment instrument which treats a treated target such as a living body tissue by using an ultrasonic vibration. In this ultrasonic treatment instrument, there are provided a plurality of piezoelectric elements which generate an ultrasonic vibration by being supplied with electric power. The ultrasonic vibration, which has been generated, is transmitted to an end effector through a waveguide. A back mass, which is a proximal-side fixing member, abuts on an elements unit including the piezoelectric elements from a proximal direction side, and a front mass, which is a distal-side fixing member, abuts on the elements unit from a distal direction side. Specifically, the elements unit (piezoelectric elements) is sandwiched between the back mass and front mass in a longitudinal direction.

BRIEF SUMMARY OF THE INVENTION

According to one aspect of the invention, a vibration generating unit includes that: an element unit including a piezoelectric element which is configured to generate an ultrasonic vibration by being supplied with electric power, the element unit having a proximal end and a distal end, and extending along a longitudinal axis from the proximal end to the distal end; a proximal-side fixing member abutting on the element unit from a proximal direction side; and a distal-side fixing member abutting on the element unit from a distal direction side, the distal-side fixing member being configured such that the element unit is sandwiched between the proximal-side fixing member and the distal-side fixing member in a longitudinal direction which is parallel to the longitudinal axis, and being configured to transmit the ultrasonic vibration, which is generated in the element unit, toward the distal direction side, the distal-side fixing member having a greater acoustic impedance than the proximal-side fixing member.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

A first embodiment of the present invention is described with reference to FIG. 1 to FIG. 9.

Figure 1:
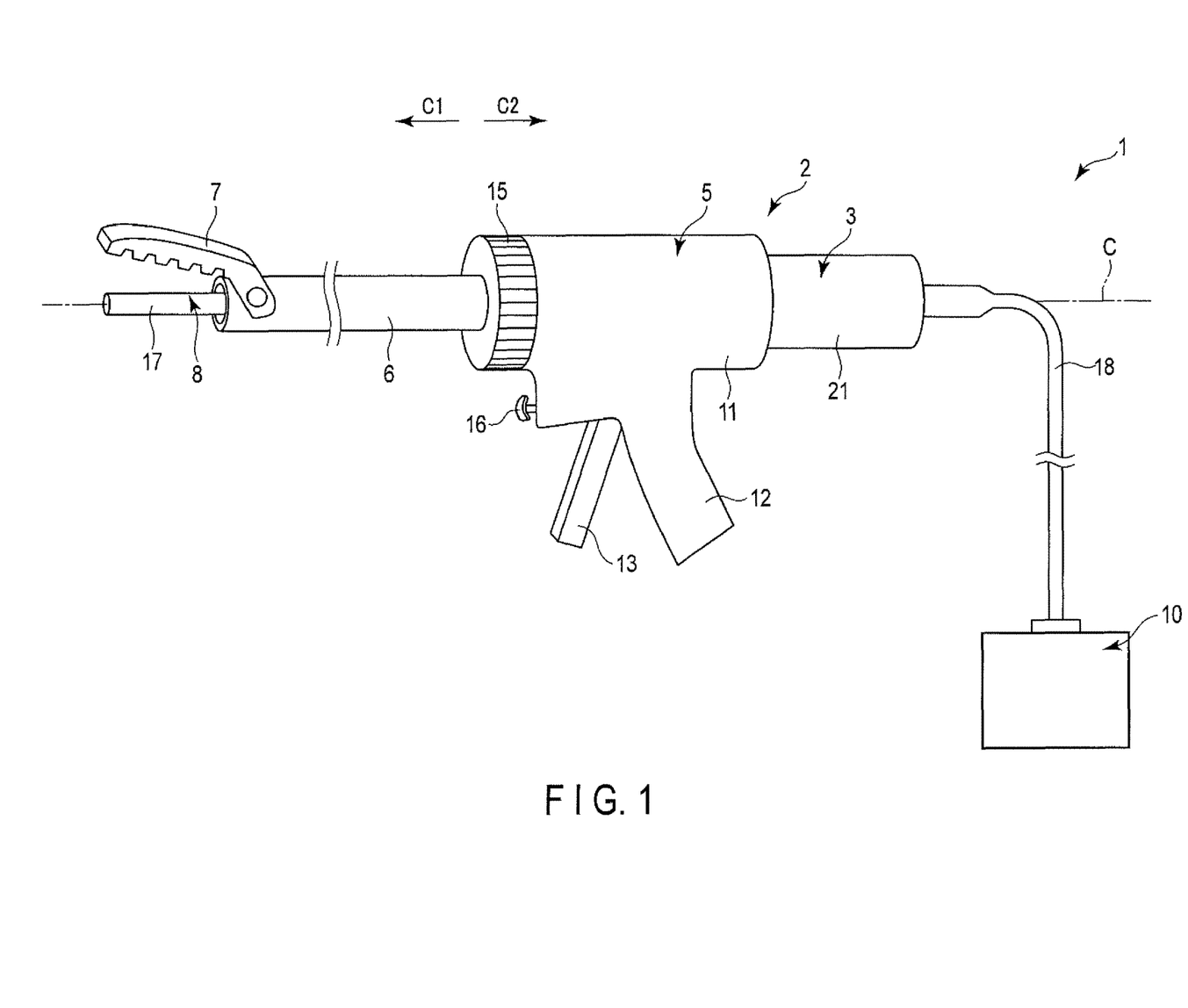
FIG. 1 is a schematic view illustrating an ultrasonic treatment system according to a first embodiment.

FIG. 1 is a view illustrating an ultrasonic treatment system 1 of the present embodiment. As illustrated in FIG. 1, the ultrasonic treatment system 1 includes an ultrasonic treatment instrument 2. The ultrasonic treatment instrument 2 has a longitudinal axis C. Here, two directions parallel to the longitudinal axis C are set as longitudinal directions. In addition, one of the longitudinal directions is a distal direction (a direction of arrow C1 in FIG. 1), and the direction opposite to the distal direction is a proximal direction (a direction of arrow C2 in FIG. 1).

The ultrasonic treatment instrument 2 includes a transducer unit 3, a holding unit 5 which can be held by a surgeon or the like, a sheath 6, a jaw (grasping member) 7, and a probe (distal vibration transmitting member) 8. The holding unit 5 includes a case body portion 11 extending along the longitudinal axis C, a stationary handle 12 which extends from the case body portion 11 toward one certain direction crossing the longitudinal axis C, and a movable handle 13 which is rotatably attached to the case body portion 11. By the movable handle 13 rotating relative to the case body portion 11, the movable handle 13 opens or closes relative to the stationary handle 12. A rotary operation knob 15, which is a rotary operation input section, is coupled to a distal direction side of the case body portion 11. The rotary operation knob 15 is rotatable about the longitudinal axis C relative to the case body portion 11. In addition, an energy operation button 16, which is an energy operation input section, is attached to the case body portion 11.

The sheath 6 is coupled to the holding unit 5 in a state in which the sheath 6 is inserted, from the distal direction side, into the inside of the rotary operation knob 15 and the inside of the case body portion 11. In addition, the jaw 7 is rotatably attached to a distal portion of the sheath 6. The probe 8 extends from the inside of the case body portion 11 toward the distal direction side through the inside of the sheath 6. In the present embodiment, the center axis of the probe 8 agrees with the longitudinal axis C, and the probe 8 extends along the longitudinal axis C from the proximal end to the distal end. A treatment section 17 is provided in a distal portion of the probe 8. The probe 8 is inserted through the sheath 6 in a state in which the treatment section 17 projects from the distal end of the sheath 6 toward the distal direction side. By opening or closing the movable handle 13, which is an opening-and-closing operation input section, relative to the stationary handle 12, a movable portion (not shown) of the sheath 6 moves along the longitudinal axis C, and the jaw 7 rotates. By the rotation of the jaw 7, the jaw 7 opens or closes relative to the treatment section 17 of the probe 8. In addition, the sheath 6, jaw 7 and probe 8, together with the rotary operation knob 15, are rotatable about the longitudinal axis C relative to the case body portion 11.

Figure 2:
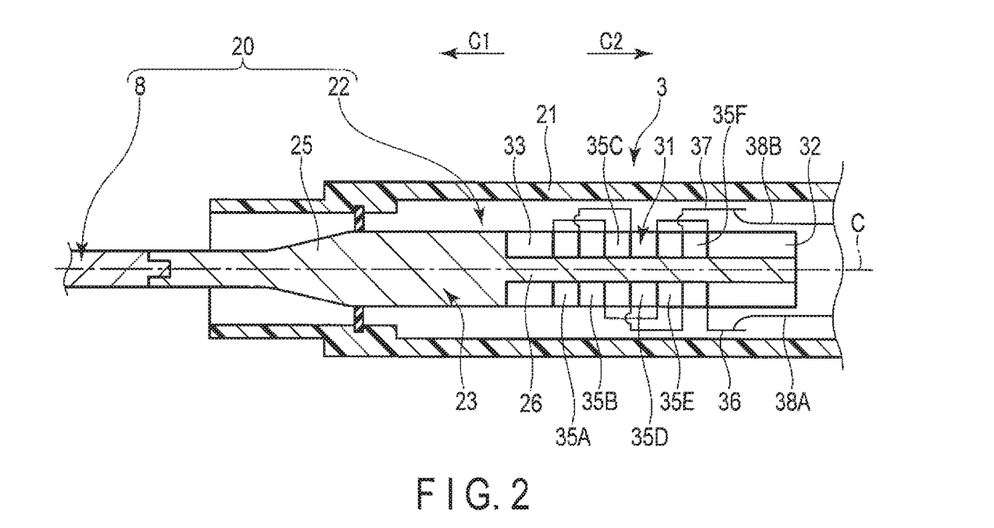
FIG. 2 is a cross-sectional view which schematically illustrates the configuration of a transducer unit according to the first embodiment.

FIG. 2 is a view illustrating the configuration of the transducer unit 3. As illustrated in FIG. 1 and FIG. 2, the oscillator unit 3 includes a transducer case 21 which forms an exterior of the transducer unit 3. The oscillator case 21 is coupled to the holding unit 5 in a state in which the transducer case 21 is inserted into the inside of the case body portion 11 from the proximal direction side. In addition, in the inside of the case body portion 11, the transducer case 21 is separably coupled to the sheath 6. One end of a cable 18 is connected to the transducer case 21. In the ultrasonic treatment system 1, the other end of the cable 18 is separably connected to an energy source unit 10. Here, the energy source unit 10 is, for example, an energy control device for medical use, and includes an electric power supply (not shown), an AC converter circuit (not shown), etc. In addition, the energy source unit 10 includes a controller (not shown) which controls an output of electric power. The controller includes a processor, which includes a CPU (Central Processing Unit) or an ASIC (application specific integrated circuit), and a storage section (not shown) such as a memory.

In addition, in the transducer unit 3, a vibration generating unit (ultrasonic transducer) 22 is provided in the inside of the oscillator case 21. The vibration generating unit 22 is supported by the transducer case 21. The vibration generating unit 22 includes a rod-shaped member (proximal vibration transmitting member) 23. In this embodiment, the center axis of the rod-shaped member 23 agrees with the longitudinal axis C, and the rod-shaped member 23 extends along the longitudinal axis C from the proximal end to the distal end. In the inside of the case body portion 11, a distal end of the rod-shaped member 23 is separably connected to the proximal end of the probe 8. By the rod-shaped member 23 being connected to the probe 8, the probe 8 is coupled to the distal direction side of the vibration generating unit 22. In the meantime, in the state in which the probe 8 is coupled to the vibration generating unit 22, the vibration generating unit 22, together with the probe 8, is rotatable about the longitudinal axis C relative to the case body portion 11.

A tapered horn (cross-section reducing portion) 25, whose cross-sectional area perpendicular to the longitudinal axis C gradually decreases toward the distal direction, is formed in the rod-shaped member 23. In addition, an elements attachment portion 26 is provided in the rod-shaped member 23 and on the proximal direction side with respect to the horn 25. In the vibration generating unit 22, an elements unit 31, a back mass 32 that is a proximal-side fixing member, and a front mass 33 that is a distal-side fixing member, are attached to the elements attachment portion 26. The elements unit 31, back mass 32 and front mass 33 are formed in annular shapes, and the elements attachment portion 26 is inserted through the front mass 33, elements unit 31 and back mass 32 in the named order, and thereby the elements unit 31, back mass 32 and front mass 33 are attached to the elements attachment portion 26.

The elements unit 31 includes a proximal end and a distal end, and extends along the longitudinal axis C from the proximal end to the distal end. In the present embodiment, the elements unit 31 is provided coaxial with the longitudinal axis C. The back mass 32 abuts on the proximal end of the elements unit 31, and the front mass 33 abuts on the distal end of the elements unit 31. In other words, the back mass 32 abuts on the elements unit 31 from the proximal direction side, and the front mass 33 abuts on the elements unit 31 from the distal direction side. Thus, the elements unit 31 is sandwiched between the back mass (proximal-side fixing member) 32 and front mass (distal-side fixing member) 33 in the longitudinal direction that is parallel to the longitudinal axis C.

Figure 3:
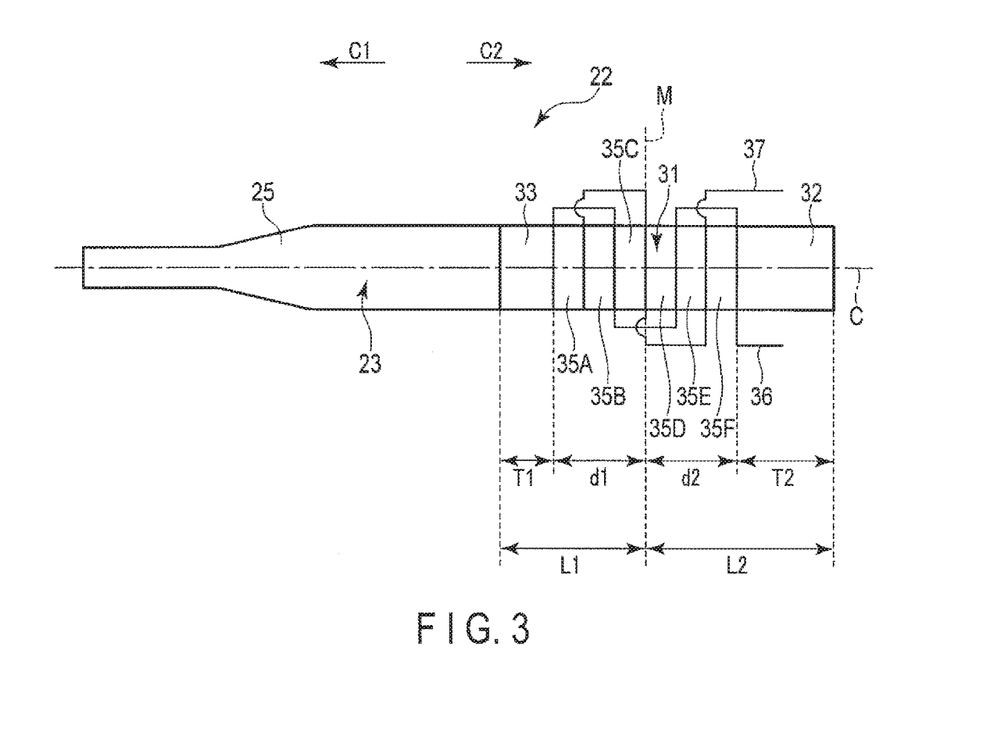
FIG. 3 is a schematic view illustrating the configuration of a vibration generating unit according to the first embodiment.

FIG. 3 is a view illustrating the configuration of the vibration generating unit 22. As illustrated in FIG. 2 and FIG. 3, the elements unit 31 includes a plurality (six in this embodiment) of piezoelectric elements 35A to 35F, a first electrode member 36, and a second electrode member 37. Each of the piezoelectric elements 35A to 35F is interposed between the first electrode member 36 and second electrode member 37 in the longitudinal direction of the vibration generating unit 22. One end of an electric wiring portion 38A is connected to the first electrode member 36, and one end of an electric wiring portion 38B is connected to the second electrode member 37. The electric wiring portions 38A and 38B extend through the inside of the cable 18, and the other end of the electric wiring portion 38A and the other end of the electric wiring portion 38B are electrically connected to the AC converter circuit (not shown) of the energy source unit 10.

In addition, a switch section (not shown) is provided in the inside of the holding unit 5. The open or closed state of the switch section is changed over in accordance with an input of an energy operation in the energy operation button 16. The switch section is electrically connected to the controller (not shown) of the energy source unit 10 via a signal path portion (not shown) which extends through the transducer unit 3 and the inside of the cable 18. By detecting open or closed state of the switch section, the controller detects an input of the energy operation in the energy operation button 16. By the input of the energy operation being detected, electric power is output from the energy source unit 10. By the electric power (AC electric power) being output from the energy source unit 10, a voltage is applied between the first electrode member 36 and second electrode member 37. By the voltage applied between the first electrode member 36 and second electrode member 37, an electric current (AC current) flows through the piezoelectric elements 35A to 35F each of which is interposed between the first electrode member 36 and second electrode member 37, and the respective piezoelectric elements 35A to 35F convert the current to an ultrasonic vibration. Specifically, in the respective piezoelectric elements 35A to 35F, an ultrasonic vibration is generated by the supply of electric power (electric energy).

The generated ultrasonic vibration is transmitted from the elements unit 31 through the front mass 33 toward the distal direction side. In addition, the ultrasonic vibration is transmitted to the probe 8 from the front mass 33 through the rod-shaped member 23. At this time, in the horn 25, the amplitude of vibration is increased. Then, in the probe 8, the ultrasonic vibration is transmitted toward the treatment section 17. The treatment section 17 treats a treated target, such as a living body tissue, by using the transmitted ultrasonic vibration. In the state in which the ultrasonic vibration is transmitted toward the treatment section 17, a vibrating body unit 20, which vibrates by the ultrasonic vibration, is formed by the vibration generating unit 22 and probe 8. In the state in which the ultrasonic vibration is transmitted toward the treatment section 17, the vibrating body unit 20 performs a longitudinal vibration, the vibration direction of which is parallel to the longitudinal axis C (longitudinal direction). In the present embodiment, the proximal end of the vibrating body unit 20 is formed by the proximal end of the back mass 32 (the proximal of the rod-shaped member 23), and the distal end of the vibrating body unit 20 is formed by the distal end of the probe 8.

In addition, a central position between the distal end and proximal end of the elements unit 31 in the longitudinal direction is set as an elements central position M. In this embodiment, the piezoelectric elements 35A to 35F are symmetrically arranged with respect to the elements central position M in the longitudinal direction. Thus, in the elements unit 31, three piezoelectric elements 35A to 35C are arranged on the distal direction side with respect to the elements central position M, and three piezoelectric elements 35D to 35F are arranged on the proximal direction side with respect to the elements central position M. Besides, since the piezoelectric elements 35A to 35F are symmetrically arranged with respect to the elements central position M, a dimension (first unit dimension) d1 from the elements central position M to the distal end of the elements unit 31 is identical (substantially identical) to a dimension (second unit dimension) d2 from the elements central position M to the proximal end of the elements unit 31.

The cross-sectional area (elements cross-sectional area) of the elements unit 31 perpendicular to the longitudinal axis C (the transmitting direction of the ultrasonic vibration) is set as S0. In addition, the cross-sectional area (first member cross-sectional area) of the front mass 33 perpendicular to the longitudinal axis C (the transmitting direction of the ultrasonic vibration) is set as S1, and the cross-sectional area (second member cross-sectional area) of the back mass 32 perpendicular to the longitudinal axis C (the transmitting direction of the ultrasonic vibration) is set as S2. In the present embodiment, the cross-sectional area S0 of the elements unit 31 is uniform with (substantially identical to) the cross-sectional area S1 of the front mass 33, and is uniform with (substantially identical to) the cross-sectional area S2 of the back mass 32. Accordingly, in this embodiment, the cross-sectional area (first member cross-sectional area) S1 of the front mass 33 is uniform with (substantially identical to) the cross-sectional area (second member cross-sectional area) S2 of the back mass 32.

Furthermore, in this embodiment, a dimension (first attachment dimension) L1 from the elements central position M of the elements unit 31 to the distal end of the front mass 33 is less than a dimension (second attachment dimension) L2 from the elements central position M to the proximal end of the back mass 32. As described above, the dimension d1 from the elements central position M to the distal end of the elements unit 31 is identical (substantially identical) to the dimension d2 from the elements central position M to the proximal end of the elements unit 31. Thus, a dimension (first member dimension) T1 of the front mass (distal-side fixing member) 33 in the longitudinal direction is less than a dimension (second member dimension) T2 of the back mass (proximal-side fixing member) 32 in the longitudinal direction.

The material, of which the piezoelectric elements 35A to 35F (elements unit 31) are formed, has an acoustic characteristic impedance (elements acoustic characteristic impedance) $\zeta 0$. In addition, the material, of which the front mass 33 is formed, has an acoustic characteristic impedance (first member acoustic characteristic impedance) $\zeta 1$, and the material, of which the back mass 32 is formed, has an acoustic characteristic impedance (second member acoustic characteristic impedance) $\zeta 2$. Here, the acoustic characteristic impedance $\zeta$ of the material (substance), of which parts are formed, is a value which is determined by a density $\rho$ of material and a propagation velocity c of sound in the material, and is defined by equation (1) by using the density $\rho$ of material and Young's modulus E.

$$\zeta = \rho \times \sqrt{\frac{E}{\rho}} = \rho \times c \qquad (1)$$

Accordingly, the acoustic characteristic impedance (characteristic impedance) $\zeta$ is a physicality value that is determined by the material of which parts are formed, and has an inherent value for each material (substance). The acoustic characteristic impedance $\zeta 0$ of the piezoelectric elements 35A to 35F (elements unit 31) is greater than each of the acoustic characteristic impedance $\zeta 1$ of the front mass 33 and the acoustic characteristic impedance $\zeta 2$ of the back mass 32. In addition, in this embodiment, the acoustic characteristic impedance $\zeta 1$ of the material, of which the front mass 33 is formed, is greater than the acoustic characteristic impedance $\zeta 2$ of the material, of which the back mass 32 is formed. Accordingly, at least either the density $\rho$ or the propagation velocity c of sound is greater in the material of which the front mass 33 is formed, than in the material of which the back mass 32 is formed. Here, as the material of which the back mass 32 is formed, there is, for instance, extra super duralumin (A7075; the density $\rho$ is $2.8 \times 10^3$ kg/m$^3$, the transmitting velocity c of sound is 5100 m/s, and the acoustic characteristic impedance $\zeta$ is $1.4 \times 10^7$ Pa·s/m). In addition, as the material of which the front mass 33 is formed, there are, for instance, 64 titanium alloy (Ti-6Al-4V; the density $\rho$ is $4.4 \times 10^3$ kg/m$^3$, the propagation velocity c of sound is 4900 m/s, and the acoustic characteristic impedance $\zeta$ is $2.2 \times 10^7$ Pa·s/m), SUS420F which is a kind of stainless steel (the density $\rho$ is $7.8 \times 10^3$ kg/m$^3$, the propagation velocity c of sound is 5300 m/s, and the acoustic characteristic impedance $\zeta$ is $4.1 \times 10^7$ Pa·s/m), and lead zirconate titanate (PZT; the density $\rho$ is $7.8 \times 10^3$ kg/m$^3$, the propagation velocity c of sound is 2900 m/s, and the acoustic characteristic impedance $\zeta$ is $2.3 \times 10^7$ Pa·s/m). Besides, when the front mass 33 is formed of SUS420F, the back mass 32 may formed of 64 titanium alloy or lead zirconate titanate.

The acoustic impedance (elements acoustic impedance) of the elements unit 31 (piezoelectric elements 35A to 35F) in a cross section perpendicular to the transmitting direction of the ultrasonic vibration (longitudinal axis C) is set as Z0. In addition, the acoustic impedance (first member acoustic impedance) of the front mass 33 in a cross section perpendicular to the transmission direction of the ultrasonic vibration is set as Z1, and the acoustic impedance (second member acoustic impedance) of the back mass 32 in a cross section perpendicular to the transmitting direction of the ultrasonic vibration is set as Z2. Here, the acoustic impedance Z in the cross section perpendicular to the transmitting direction of the ultrasonic vibration is defined by equation (2) by using the acoustic characteristic impedance $\zeta$, which is a physicality value, and the cross-sectional area S of parts perpendicular to the transmitting direction of the ultrasonic vibration.

$$Z = \zeta \times S \quad (2)$$

In the elements unit 31, back mass 32 and front mass 33, the acoustic characteristic impedance $\zeta$ and the cross-sectional area S are set as described above. Thus, the acoustic impedance Z0 of the elements unit 31 (piezoelectric elements 35A to 35F) in the cross section perpendicular to the transmitting direction of the ultrasonic vibration is greater than each of the acoustic impedance Z1 of the front mass 33 and the acoustic impedance Z2 of the back mass 32. In addition, in this embodiment, the acoustic impedance Z1 of the front mass 33 in the cross section perpendicular to the transmission direction of the ultrasonic vibration is greater than the acoustic impedance Z2 of the back mass 32 in the cross section perpendicular to the transmitting direction of the ultrasonic vibration. Incidentally, the acoustic characteristic impedance $\zeta$ agrees with the value of the acoustic impedance Z per unit area (unit cross-sectional area).

Next, the functions and advantageous effects of the vibration generating unit 22, vibrating body unit 20 and ultrasonic treatment instrument 2 of the present embodiment are described. When treatment is performed by using the ultrasonic treatment instrument 2, the sheath 6, jaw 7 and probe 8 are inserted into the body in the state in which the holding unit 5 is held. Then, a treated target, such as a living body tissue, is disposed between the jaw 7 and the treatment section 17 of probe 8. In this state, the movable handle 13 is closed relative to the stationary handle 12, and the jaw 7 is closed relative to the treatment section 17. Thereby, the treated target is grasped between the jaw 7 and the treatment section 17. In the state in which the treated target is gripped, an energy operation is input by the energy operation button 16. Thereby, electric power is output from the energy source unit 10, and the output electric power is supplied to the piezoelectric elements 35A to 35F of the vibration generating unit 22. Thereby, an ultrasonic vibration is generated by the piezoelectric elements 35A to 35F (elements unit 31). Then, the generated ultrasonic vibration is transmitted to the probe 8 through the front mass 33 and rod-shaped member 23, and the ultrasonic vibration is transmitted in the probe 8 toward the treatment section 17. Thereby, the vibrating body unit 20, which is composed of the vibration generating unit 22 and probe 8, performs a longitudinal vibration, the vibrating direction of which is parallel to the longitudinal axis C. By the treatment section 17 vibrating longitudinally in the state in which the treated target is grasped between the jaw 7 and treatment section 17, frictional heat occurs between the treatment section 17 and the treated target. By the frictional heat, the treated target is coagulated and cut at the same time.

In the treatment, the frequency of electric current, the current value, the voltage value, etc. of the electric power, which is supplied to the piezoelectric elements 35A to 35F, are adjusted by the controller of the energy source unit 10. In addition, the vibrating body unit 20 is designed in such a state that the vibrating body unit 20 vibrates at a predetermined frequency Frref (e.g. 47 kHz) by the ultrasonic vibration caused by the piezoelectric elements 35A to 35F. In the vibrating body unit 20, the vibration generating unit 22, which includes expensive piezoelectric elements 35A to 35F, is subjected to sterilization processing, etc. after use, and is re-used. On the other hand, the probe 8 is discarded after use. Here, in the process of manufacturing the probe 8 of a material such as titanium material, a variation tends to easily occur in physicality of the material (in particular, Young's modulus). Thus, a variance occurs in physicality of material among manufactured probes 8. With the variance occurring in physicality of material among the manufactured probes 8, a resonance frequency Fr in a state in which the vibrating body unit 20 vibrates varies in the vibrating body unit 20 in accordance with the physicality of the material of the probe 8 which is connected to the vibration generating unit 22. Specifically, in the vibrating body unit 20, a variance occurs in the resonance frequency Fr of vibration in accordance with the physicality of the material, and the vibrating body unit 20 does not necessarily vibrate at the predetermined frequency Frref. Accordingly, by the ultrasonic vibration generated by the piezoelectric elements 35A to 35F, the vibrating body unit 20 vibrates in a predetermined frequency range $\Delta f$ between a minimum resonance frequency Frmin (e.g. 46 kHz) and a maximum resonance frequency Frmax (e.g. 48 kHz). Incidentally, the predetermined frequency Frref is included in the predetermined frequency range $\Delta f$.

Figure 4:
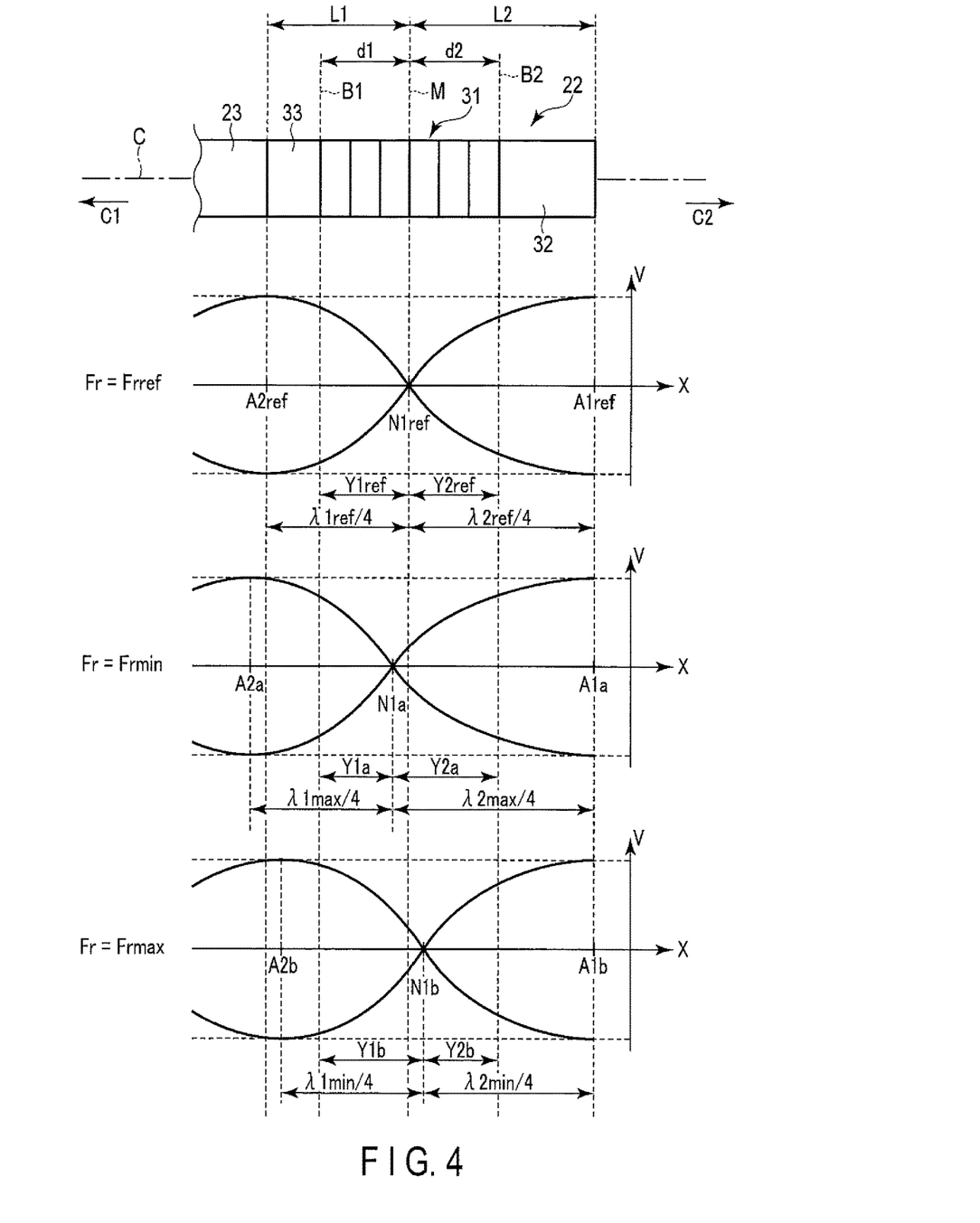
FIG. 4 is a schematic view for explaining a longitudinal vibration in the vibration generating unit in a state in which a vibrating body unit according to the first embodiment is longitudinally vibrating in a predetermined frequency range.

FIG. 4 is a view for explaining a longitudinal vibration (vibration) in the vibration generating unit 22 in a state in which the vibrating body unit 20 is longitudinally vibrating in the predetermined frequency range $\Delta f$. FIG. 4 shows graphs illustrating a state of the longitudinal vibration at the predetermined frequency Frref, a state of the longitudinal vibration at the minimum resonance frequency Frmin, and a state of the longitudinal vibration at the maximum resonance frequency Frmax. In these graphs, the abscissa indicates a position (X) in the longitudinal direction, and the ordinate indicates a vibration state (V) of longitudinal vibration. In the state in which the vibrating body unit 20 is longitudinally vibrating, the distal end and proximal end of the vibrating body unit 20 become free ends. Thus, one of antinode positions of longitudinal vibration is located at the proximal end of the vibrating body unit 20 (the proximal end of the back mass 32), and another of the antinode positions of longitudinal vibration is located at the distal end of the vibrating body unit 20 (the distal end of the probe 8). As illustrated in FIG. 4, in the state in which the vibrating body unit 20 longitudinally vibrates in the predetermined frequency range Δf, an antinode position A1 (indicated by A1ref, A1a and A1b in FIG. 4), which is one of the antinode positions of longitudinal vibration, is located at the proximal end of the back mass 32. In the present embodiment, the antinode position A1 becomes a most proximal antinode position which is located most proximally among the antinode positions of the longitudinal vibration.

Here, a node position, which is located on the distal direction side by a ¼ wavelength (λ/4) of the longitudinal vibration relative to the antinode position A1, is set as a node position N1, and an antinode position, which is located on the distal direction side by a ½ wavelength (λ/2) of the longitudinal vibration relative to the antinode position A1, is set as an antinode position A2. The node position N1 (indicated by N1ref, N1a and N1b in FIG. 4) is a most proximal node position which is located most proximally among the node positions of the longitudinal vibration, and the antinode position A2 (indicated by A2ref, A2a and A2b in FIG. 4) is located second proximally among the antinode positions of longitudinal vibration. In the state in which the vibrating body unit 20 vibrates at the predetermined resonance frequency Frref, the node position N1ref is located at the elements central position M that is the central position between the distal end and proximal end of the elements unit 31 in the longitudinal direction. In addition, in the state in which the vibrating body unit 20 vibrates at the predetermined resonance frequency Frref, the antinode position A2ref is located at the distal end of the front mass 33. In the meantime, a wavelength λ of the longitudinal vibration in the state in which the resonance frequency Fr is the predetermined reference frequency Frref is set as a reference wavelength λref.

As the resonance frequency decreases from the predetermined resonance frequency Frref, the wavelength λ of the longitudinal vibration increases from the reference wavelength λref. Accordingly, in the vibration of the vibrating body unit 20 in the predetermined frequency range Δf, when the resonance frequency Fr becomes the minimum resonance frequency Frmin, the wavelength λ becomes a maximum wavelength λmax. Thus, in the state in which the resonance frequency Fr becomes the minimum resonance frequency Frmin, the antinode position A1a is located at the proximal end of the back mass 32, but the node position N1a is located on the distal direction side with respect to the elements center position M and the antinode position A2a is located on the distal direction side with respect to the distal end of the front mass 33. However, even in the case in which the resonance frequency Fr becomes the minimum resonance frequency Frmin, the node position N1a is located on the proximal direction side with respect to the proximal end of the front mass 33 and is located within the range in which the elements unit 31 extends in the longitudinal direction. On the other hand, as the resonance frequency increases from the predetermined resonance frequency Frref, the wavelength λ of the longitudinal vibration decreases from the reference wavelength λref. Accordingly, in the vibration of the vibrating body unit 20 in the predetermined frequency range Δf, when the resonance frequency Fr becomes the maximum resonance frequency Frmax, the wavelength λ becomes a minimum wavelength λmin. Thus, in the state in which the resonance frequency Fr becomes the maximum resonance frequency Frmax, the antinode position A1b is located at the proximal end of the back mass 32, but the node position N1b is located on the proximal direction side with respect to the elements central position M and the antinode position A2b is located on the proximal direction side with respect to the distal end of the front mass 33. However, even in the case in which the resonance frequency Fr becomes the maximum resonance frequency Frmax, the node position N1b is located on the distal direction side with respect to the distal end of the back mass 32 and is located within the range in which the elements unit 31 extends in the longitudinal direction.

As described above, in the state in which the vibrating body unit 20 vibrates in the predetermined frequency range Δf, the node position N1 (indicated by N1ref, N1a and N1b in FIG. 4) is located on the distal direction side by the ¼ wavelength (λ/4) of the longitudinal vibration relative to the antinode position A1 which is located at the proximal end of the back mass 32, and the node position N1 is located within the range in which the elements unit 31 extends in the longitudinal direction. In addition, in the state in which the vibrating body unit vibrates in the predetermined frequency range Δf, the antinode position A2 (indicated by A2ref, A2a and A2b in FIG. 4) is located on the distal direction side by the ½ wavelength (λ/2) of the longitudinal vibration relative to the antinode position A1 that is located at the proximal end of the back mass 32, and the antinode position A2 is located on the distal direction side with respect to the distal end of the elements unit 31 (the proximal end of the front mass 33). Accordingly, in the longitudinal vibration of any resonance frequency Fr in the predetermined frequency range Δf, only the node position (reference node position) N1, among the antinode positions and node positions of the longitudinal vibration, is located between the proximal end and distal end of the elements unit 31 in the longitudinal direction.

In addition, in the present embodiment, as described above, the acoustic characteristic impedance $\zeta_1$ of the material, of which the front mass 33 is formed, is greater than the acoustic characteristic impedance $\zeta_2$ of the material, of which the back mass 32 is formed. Hence, the acoustic impedance Z in the cross section perpendicular to the transmitting direction of the ultrasonic vibration (longitudinal axis C) is greater in the front mass 33 than in the back mass 32. Since the acoustic impedance Z1 of the front mass 33 becomes greater than the acoustic impedance Z2 of the back mass 32, a length λ1/4 (indicated by λ1ref/4, λ1max/4 and λ1min/4 in FIG. 4) corresponding to the ¼ wavelength of the longitudinal vibration between the antinode position A2 and node position N1 becomes, in the longitudinal vibration at any resonance frequency Fr in the predetermined frequency range Δf, smaller than a length λ2/4 (indicated by λ2ref/4, λ2max/4 and λ2min/4 in FIG. 4) corresponding to the ¼ wavelength of the longitudinal vibration between the antinode position A1 and node position N1. Specifically, in the state in which the vibrating body unit 20 vibrates in the predetermined frequency range Δf, the length (first length) λ1/4 corresponding to the ¼ wavelength of the longitudinal vibration from the node position (reference node position) N1 toward the distal direction side becomes smaller than the length (second length) λ2/4 corresponding to the ¼ wavelength of the longitudinal vibration from the node position (reference node position) N1 toward the proximal direction side. In the state in which the vibrating body unit 20 vibrates at the predetermined frequency Frref, the length (first length) λ1ref/4 corresponding to the ¼ wavelength of longitudinal vibration from the node position N1 toward the distal direction side agrees with the dimension (first attachment dimension) L1 from the elements central position M of the elements unit 31 to the distal end of the front mass 33, and the length (second length) λ2ref/4 corresponding to the ¼ wavelength of longitudinal vibration from the node position N1 toward the proximal direction side agrees with the dimension (second attachment dimension) L2 from the elements central position M of the elements unit 31 to the proximal end of the back mass 32.

In addition, in the present embodiment, as described above, at a boundary (first boundary) B1 between the elements unit 31 and front mass 33 and at a boundary (second boundary) B2 between the elements unit 31 and back mass 32, the acoustic characteristic impedance ζ of the material, of which parts are formed, varies, and the acoustic impedance Z in the cross section perpendicular to the transmitting direction of the ultrasonic vibration varies. Thus, in the state in which the vibrating body unit 20 vibrates by the ultrasonic vibration, the amplitude of the longitudinal vibration varies between the back mass 32 and elements unit 31, and the amplitude of the longitudinal vibration varies between the elements unit 31 and front mass 33. Since the acoustic impedance Z (acoustic characteristic impedance ζ) becomes smaller in the front mass 33 than in the elements unit 31, the amplitude of the longitudinal vibration is increased in the front mass 33 relative to the elements unit 31, and a transformation ratio (first transformation ratio) ε1 of the amplitude in the front mass (distal-side fixing member) 33 relative to the amplitude in the elements unit 31 becomes greater than 1. On the other hand, since the acoustic impedance Z (acoustic characteristic impedance ζ) becomes greater in the elements unit 31 than in the back mass 32, the amplitude of the longitudinal vibration is decreased in the elements unit 31 relative to the back mass 32, and a transformation ratio (second transformation ratio) ε2 of the amplitude in the elements unit 31 relative to the amplitude in the back mass (proximal-side fixing member) 32 becomes less than 1. In the meantime, it is preferable that the amplitude of the longitudinal vibration in the front mass 33 becomes equal to the amplitude of the longitudinal vibration in the back mass 32, by the amplitude being decreased at the boundary (second boundary) B2 between the elements unit 31 and back mass 32, and by the amplitude being increased at the boundary (first boundary) B1 between the elements unit 31 and front mass 33.

Figure 5:
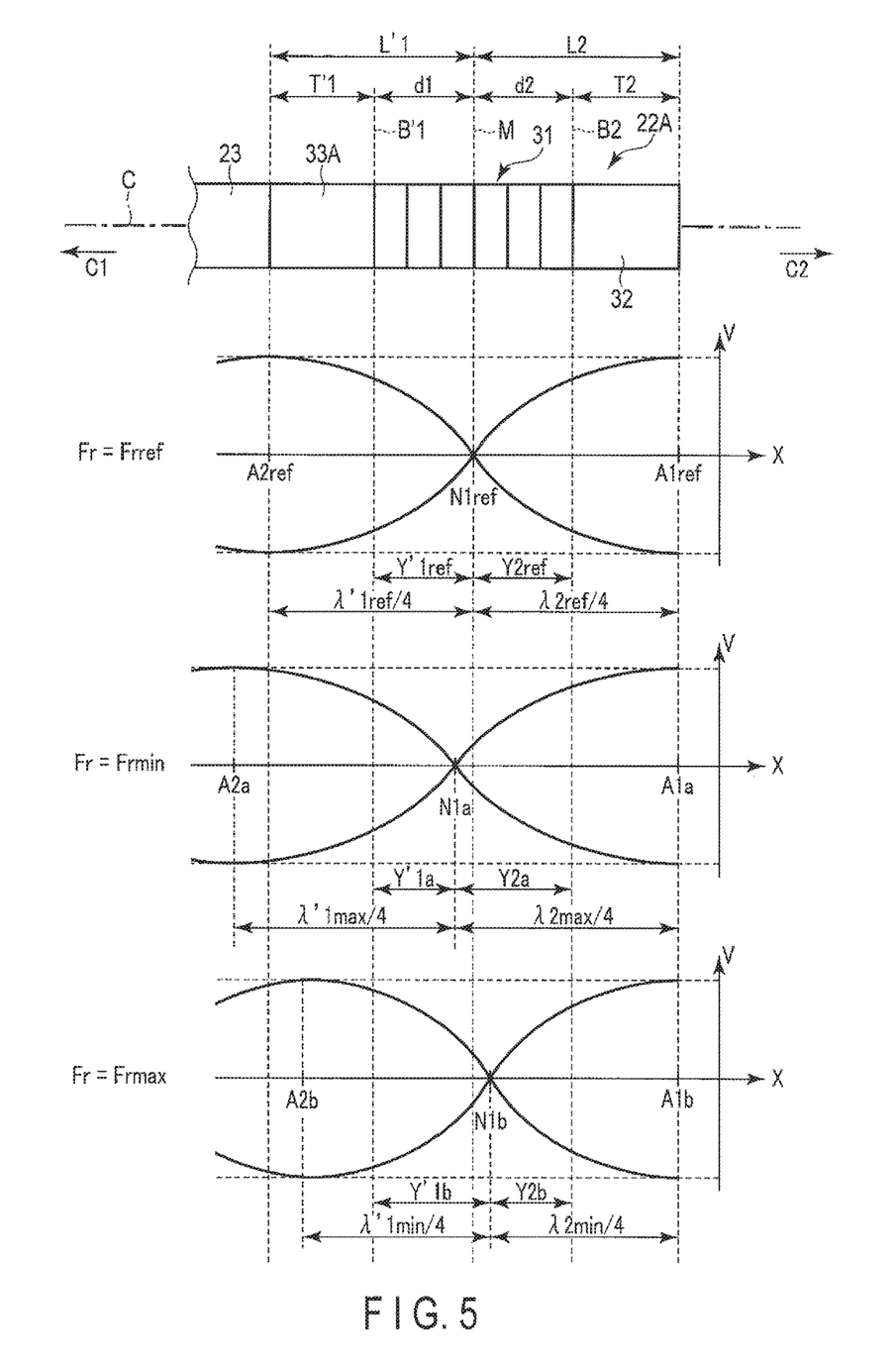
FIG. 5 is a schematic view for explaining a longitudinal vibration in a vibration generating unit in a state in which a vibrating body unit according to a comparative example is longitudinally vibrating in a predetermined frequency range.

Here, as a comparative example, a vibration generating unit 22A illustrated in FIG. 5 is described. FIG. 5 illustrates a longitudinal vibration in the vibration generating unit 22A in a state in which a vibrating body unit, which is composed of the vibration generating unit 22A according to the comparative example and the probe 8, longitudinally vibrates in the predetermined frequency range Δf. FIG. 5 shows graphs illustrating a state of the longitudinal vibration at the predetermined frequency Frref, a state of the longitudinal vibration at the minimum resonance frequency Frmin, and a state of the longitudinal vibration at the maximum resonance frequency Frmax. In these graphs, the abscissa indicates a position (X) in the longitudinal direction, and the ordinate indicates a vibration state (V) of the longitudinal vibration. As illustrated in FIG. 5, in the vibration generating unit 22A according to the comparative example, there are provided the rod-shaped member 23, elements unit 31 and back mass 32, which have the same structures as in the vibration generating unit 22 of the first embodiment. However, in the comparative example, a front mass 33A is provided in place of the front mass 33 of the first embodiment. In the comparative example, a dimension T'1 of the front mass (distal-side fixing member) 33A in the longitudinal direction is identical to the dimension T2 of the back mass 32 in the longitudinal direction. Accordingly, a dimension L'1 from the elements central position M of the elements unit 31 to the distal end of the front mass 33A is identical to the dimension L2 from the elements central position M to the proximal end of the back mass 32. In addition, in the comparative example, the acoustic characteristic impedance ζ of material and the cross-sectional area S perpendicular to the longitudinal axis C in the front mass 33A are identical to those in the back mass 32. Accordingly, an acoustic impedance Z'1 of the front mass 33A is identical to the acoustic impedance Z2 of the back mass 32.

Because of the above-described structure, in the comparative example, a length A'1/4 (indicated by λ'1ref/4, λ'1max/4 and λ'1min/4 in FIG. 5) corresponding to a ¼ wavelength of the longitudinal vibration between the antinode position A2 (indicated by A2ref, A2a and A2b in FIG. 5) and node position N1 (indicated by N1ref, N1a and N1b in FIG. 5) is, in the longitudinal vibration at any resonance frequency Fr in the predetermined frequency range Δf, identical to the length λ2/4 (indicated by λ2ref/4, λ2max/4 and λ2min/4 in FIG. 5) corresponding to a ¼ wavelength of the longitudinal vibration between the antinode position A1 (indicated by A1ref, A1a and A1b in FIG. 5) and node position N1. Specifically, in the comparative example, in the state in which the vibrating body unit 20 vibrates in the predetermined frequency range Δf, the length (first length) A'1/4 corresponding to the ¼ wavelength of the longitudinal vibration from the node position N1 toward the distal direction side becomes identical to the length λ2/4 corresponding to the ¼ wavelength of the longitudinal vibration from the node position N1 toward the proximal direction side. In addition, in the state in which the vibrating body unit 20 vibrates at the predetermined frequency Frref, the length λ'1ref/4 corresponding to the ¼ wavelength of the longitudinal vibration from the node position N1ref toward the distal direction side agrees with the dimension L'1 from the elements central position M of the elements unit 31 to the distal end of the front mass 33A, and the length λ2ref/4 corresponding to the ¼ wavelength of the longitudinal vibration from the node position N1ref toward the proximal direction side agrees with the dimension L2 from the elements central position M of the elements unit 31 to the proximal end of the back mass 32.

Here, in the first embodiment, the ratio of a distance Y1 (indicated by Y1ref, Y1a and Y1b in FIG. 4) from the node position N1 to the boundary B1 between the elements unit 31 and front mass 33 relative to the length λ1/4 corresponding to the ¼ wavelength of the longitudinal vibration from the node position (reference node position) N1 toward the distal direction side is set as a distance rate (first distance rate) ξ1. In addition, in the comparative example, the ratio of a distance Y'1 (indicated by Y'1ref, Y'1a and Y'1b in FIG. 5) from the node position N1 to a boundary B'1 between the elements unit 31 and front mass 33A relative to the length A'1/4 corresponding to the ¼ wavelength of the longitudinal vibration from the node position N1 toward the distal direction side is set as a distance rate (comparative first distance rate) ξ'1. Furthermore, in the comparative example, the ratio of the amplitude in the front mass (distal-side fixing member) 33A relative to the amplitude in the elements unit 31 is set as a transformation ratio (comparative transformation ratio) ε'1. Besides, in the first embodiment and comparative example, the ratio of a distance Y2 (indicated by Y2ref, Y2a and Y2b in FIG. 4 and FIG. 5) from the node position N1 to the boundary B2 between the elements unit 31 and back mass 32 relative to the length λ2/4 corresponding to the ¼ wavelength of the longitudinal vibration from the node position (reference node position) N1 toward the proximal direction side is set as a distance rate (second distance rate) ξ2.

Figure 6:
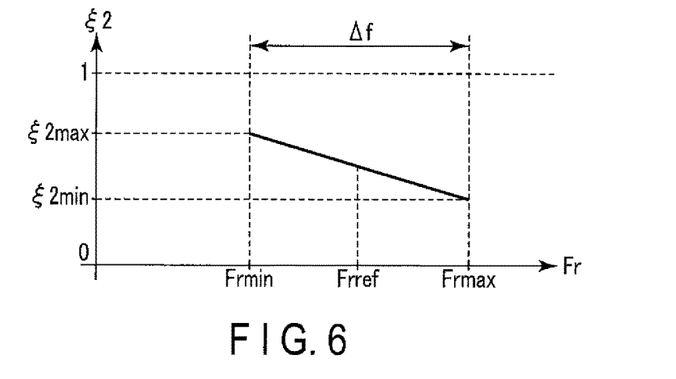
FIG. 6 is a schematic view illustrating a relation of a second distance rate relative to a resonance frequency in a case in which the resonance frequency varies in a predetermined frequency range in the first embodiment and the comparative example.
Figure 7:
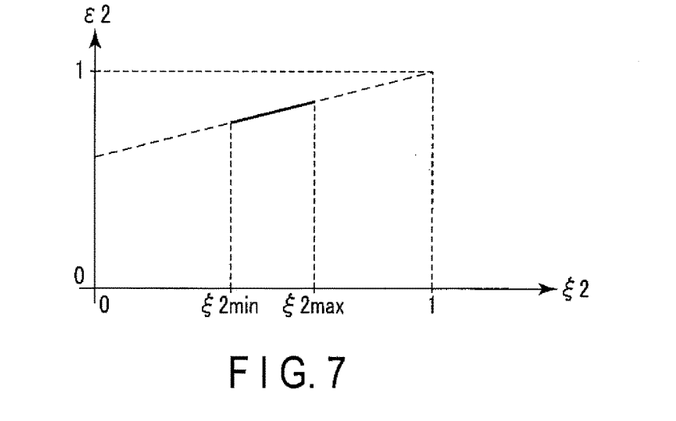
FIG. 7 is a schematic view illustrating a relation of a second transformation ratio relative to the second distance rate in the first embodiment and the comparative example.
Figure 8:
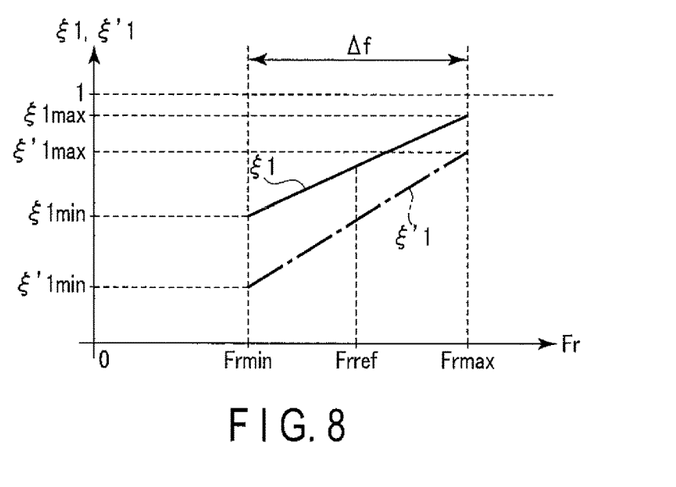
FIG. 8 is a schematic view illustrating a relation of a first distance rate relative to the resonance frequency in a case in which the resonance frequency varies in the predetermined frequency range in the first embodiment, and a relation of a comparative distance rate relative to the resonance frequency in a case in which the resonance frequency varies in the predetermined frequency range in the comparative example.
Figure 9:
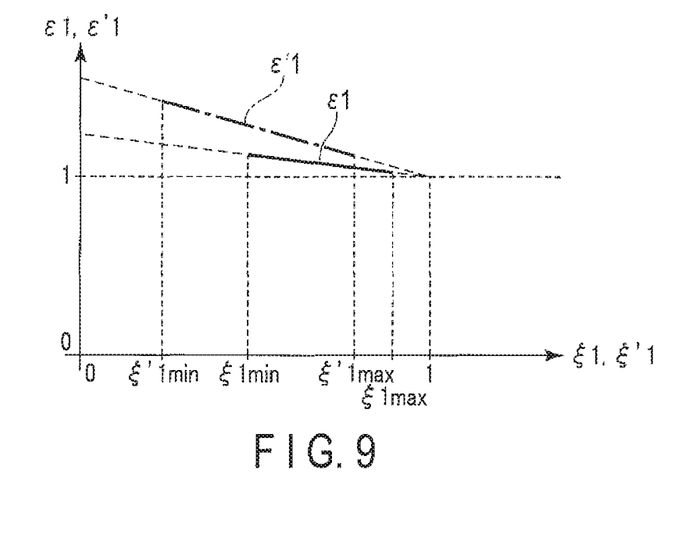
FIG. 9 is a schematic view illustrating a relation of a first transformation ratio relative to the first distance rate in the first embodiment, and a relation of a comparative transformation ratio relative to the comparative distance rate in the comparative example.

FIG. 6 illustrates a relation of the second distance rate ξ2 relative to the resonance frequency Fr in a case in which the resonance frequency Fr varies in the predetermined frequency range Δf in the first embodiment and the comparative example. FIG. 7 illustrates a relation of the second transformation ratio E2 relative to the second distance rate ξ2 in the first embodiment and the comparative example. The variation of the second distance rate ξ2 in FIG. 6 and the variation of the second transformation ratio ε2 in FIG. 7 are equal between the first embodiment and the comparative example. In FIG. 6, the abscissa indicates the resonance frequency (Fr), and the ordinate indicates the second distance rate (ξ2). In FIG. 7, the abscissa indicates the second distance rate (ξ2), and the ordinate indicates the second transformation ratio (ε2). In addition, FIG. 8 illustrates a relation of the first distance rate ξ1 relative to the resonance frequency Fr in a case in which the resonance frequency Fr varies in the predetermined frequency range Δf in the first embodiment, and a relation of the comparative distance rate ξ'1 relative to the resonance frequency Fr in a case in which the resonance frequency Fr varies in the predetermined frequency range Δf in the comparative example. FIG. 9 illustrates a relation of the first transformation ratio ε1 relative to the first distance rate ξ1 in the first embodiment, and a relation of the comparative transformation ratio ε'1 relative to the comparative distance rate ξ'1 in the comparative example. In FIG. 8, the abscissa indicates the resonance frequency (Fr), and the ordinate indicates the first distance rate (ξ1) and comparative distance rate (ξ'1). In addition, the variation of the first distance rate ξ1 is indicated by a solid line, and the variation of the comparative distance rate ξ'1 is indicated by a dot-and-dash line. Besides, in FIG. 9, the abscissa indicates the first distance rate (ξ1) and comparative distance rate (ξ'1), and the ordinate indicates the first transformation ratio (ε'1) and comparative transformation ratio (ε'1). In addition, the variation of the first transformation ratio ε1 is indicated by a solid line, and the variation of the comparative transformation ratio ε'1 is indicated by a dot-and-dash line.

As illustrated in FIG. 4 to FIG. 6, in the first embodiment and comparative example, when the vibrating body unit 20 vibrates in the predetermined frequency range Δf, the wavelength λ of the longitudinal vibration becomes smaller and the second distance rate ξ2 becomes smaller, as the resonance frequency Fr increases. For example, at a time of vibration at the maximum resonance frequency Frmax, the second distance rate ξ2 decreases to a minimum value ⅘. At a time of vibration at the minimum resonance frequency Frmin, the second distance rate ξ2 increases to a maximum value 4/7. In addition, for example, at a time of vibration at the predetermined resonance frequency Frref, the second distance rate ξ2 becomes ½. In FIG. 6, the maximum value of the second distance rate ξ2 is indicated by ξ2max, and the minimum value of the second distance rate ξ2 is indicated by ξ2min. Furthermore, as illustrated in FIG. 7, as the second distance rate ξ2 increases, the node position (reference node position) N1 shifts away from the boundary B2 between the back mass 32 and elements unit 31, and the second trans-formation ratio ε2 becomes closer to 1. Since the second transformation ratio ε2 is a value less than 1, the second transformation ratio E2 increases as the second distance rate ξ2 becomes greater.

Here, even if the resonance frequency Fr varies, the antinode position (most proximal antinode position) A1 of the longitudinal vibration is located at the proximal end of the back mass 32. Thus, even if the resonance frequency Fr varies in accordance with the probe 8 that is connected, the variance of the second distance rate ξ2 becomes small. Since the variance of the second distance rate ξ2 becomes small, the variance of the second transformation ratio ε2 at the boundary B2 between the back mass 32 and elements unit 31 can also be decreased.

As illustrated in FIG. 4, FIG. 5 and FIG. 8, in the first embodiment and comparative example, when the vibrating body unit 20 vibrates in the predetermined frequency range Δf, the wavelength λ of the longitudinal vibration becomes smaller and the first distance rate ξ1 and comparative distance rate ξ'1 become greater, as the resonance frequency Fr increases. Here, even if the resonance frequency Fr varies, the antinode position (most proximal antinode position) A1 of the longitudinal vibration is located at the proximal end of the back mass 32. Thus, in the comparative example in which the acoustic impedance Z is identical between the back mass 32 and front mass 33A, the variance of the comparative distance rate ξ'1 become greater than the variance of the second distance rate ξ'1. For example, at a time of the vibration at the maximum resonance frequency Frmax, the comparative distance rate ξ'1 increases to a maximum value ⅘. At a time of the vibration at the minimum resonance frequency Frmin, the comparative distance rate ξ'1 decreases to a minimum value ⅓. In addition, for example, at a time of the vibration at the predetermined resonance frequency Frref, the comparative distance rate ξ1 becomes ½. In FIG. 8, the maximum value of the comparative distance rate ξ'1 is indicated by ξ'max, and the minimum value thereof is indicated by ξ'1min.

Furthermore, as illustrated in FIG. 9, as the comparative distance rate ξ'1 increases, the node position (reference node position) N1 shifts away from the boundary B'1 between the front mass 33A and elements unit 31, and the comparative transformation ratio ε'1 becomes closer to 1. Since the comparative transformation ratio ε'1 is a value greater than 1, the comparative transformation ratio ε'1 decreases as the comparative distance rate ξ'1 becomes greater. Here, in the comparative example, since the variance of the comparative distance rate ξ'1 becomes greater, the variance of the comparative transformation ratio ε'1 at the boundary B'1 between the front mass 33A and elements unit 31 also becomes greater. Due to the variance of the comparative transformation ratio ε'1, the variance of the amplitude of the longitudinal vibration in the probe 8 (i.e. the part located on the distal side with respect to the front mass 33A) also becomes greater.

Thus, in the present embodiment, the acoustic impedance Z1 of the front mass 33 is made greater than the acoustic impedance Z2 of the back mass 32, and the configuration is changed from the comparative example. In the present embodiment, too, as the first distance rate ξ1 increases, the node position (reference node position) N1 shifts away from the boundary B1 between the front mass 33 and elements unit 31, and the first transformation ratio ε1 becomes closer to 1. Since the first transformation ratio ε1 is a value greater than 1, the first transformation ratio ε1 decreases as the first distance rate ξ1 becomes greater. Here, in the first embodiment and comparative example, the ratio of the acoustic impedance ($Z1$; $Z'1$) of the front mass (33; 33A) relative to the acoustic impedance $Z0$ of the elements unit 31 is set as an impedance ratio η. In the present embodiment, the acoustic impedance $Z$ (acoustic characteristic impedance ζ) is made greater in the front mass 33 than in the back mass 32. In the comparative example, the acoustic impedance $Z'1$ of the front mass 33A is identical to the acoustic impedance $Z2$ of the back mass 32. Thus, the acoustic impedance $Z1$ of the front mass 33 becomes greater than the acoustic impedance $Z'1$ of the front mass 33A in the comparative example, and the impedance ratio η becomes greater in the first embodiment than in the comparative example.

In addition, the ratio of the variation amount of the first transformation ratio $\varepsilon 1$ relative to the variation amount of the first distance rate $\xi 1$ in the present embodiment, and the ratio of the variation amount of the comparative transformation ratio $\varepsilon'1$ relative to the variation amount of the comparative distance rate $\xi'1$ in the comparative example, are each set as a variation amount ratio α. The variation amount ratio α is indicative of an absolute value of an inclination in each of the variation of the first transformation ratio $\varepsilon 1$ and the variation of the comparative transformation ratio $\varepsilon'1$ in FIG. 9. The variation amount ratio α becomes smaller as the impedance ratio η becomes greater, that is, as the difference between the acoustic impedance ($Z1$; $Z'1$) of the front mass (33; 33A) and the acoustic impedance $Z0$ of the elements unit 31 becomes smaller. Accordingly, a variation amount ratio $\alpha 1$ of the variation amount of the first transformation ratio $\varepsilon 1$ relative to the variation amount of the first distance rate $\xi 1$ in the present embodiment becomes smaller than a variation amount ratio $\alpha'1$ of the variation amount of the comparative transformation ratio $\varepsilon'1$ relative to the variation amount of the comparative distance rate $\xi'1$ in the comparative example. In fact, in FIG. 9, an inclination ($-\alpha 1$) of the variation of the first transformation ratio $\varepsilon 1$ is closer to 0 than an inclination ($-\alpha'1$) of the variation of the comparative transformation ratio $\varepsilon'1$.

As described above, in the present embodiment, by making the acoustic impedance $Z$ (acoustic characteristic impedance ζ) greater in the front mass 33 than in the back mass 32, the variation amount ratio $\alpha 1$ of the variation amount of the first transformation ratio $\varepsilon 1$ relative to the variation amount of the first distance rate $\xi 1$ becomes smaller. Accordingly, even if the resonance frequency Fr varies in accordance with the probe 8 that is connected and hence the variation occurs in the first distance rate $\xi 1$, it is possible to decrease the variation of the first transformation ratio $\varepsilon 1$ at the boundary B1 between the front mass 33 and elements unit 31.

Additionally, in this embodiment, since the acoustic impedance $Z$ becomes greater in the front mass 33 than in the back mass 32, the length $\lambda 1/4$ corresponding to the ¼ wavelength of the longitudinal vibration between the antinode position A2 and node position N1 becomes, in the longitudinal vibration at any resonance frequency Fr in the predetermined frequency range Δf, smaller than the length $\lambda 2/4$ corresponding to the ¼ wavelength of the longitudinal vibration between the antinode position A1 and node position N1. Thus, as illustrated in FIG. 8, in the longitudinal vibration at any resonance frequency Fr in the predetermined frequency range Δf, the first distance rate $\xi 1$ of the present embodiment becomes greater than the comparative distance rate $\xi'1$ of the comparative example. Specifically, in a region where the first distance rate $\xi 1$ varies in accordance with the variation of the resonance frequency Fr in the predetermined frequency range Δf, compared to a region where the comparative distance rate $\xi'1$ of the comparative example varies, the value becomes closer to 1 (the value increases). For example, at a time of the vibration at the maximum resonance frequency Frmax, the first distance rate $\xi 1$ increases to a maximum value 9/10. At a time of the vibration at the minimum resonance frequency Frmin, the first distance rate $\xi 1$ decreases to a minimum value ½. In addition, for example, at a time of the vibration at the predetermined resonance frequency Frref, the first distance rate $\xi 1$ becomes ⅔. In the present embodiment, since the region where the first distance rate $\xi 1$ varies in accordance with the variation of the resonance frequency Fr in the predetermined frequency range Δf becomes closer to 1, the variation of the first distance rate $\xi 1$ becomes smaller than the variation of the comparative distance rate $\xi'1$ of the comparative example. For example, the comparative distance rate $\xi'1$ of the comparative example varies in a range between ⅓ and ⅘, whereas the first distance rate $\xi 1$ of the present embodiment varies in a range between ½ and 9/10. In the present embodiment, since the variance of the first distance rate $\xi 1$ becomes smaller, the variance of the first transformation ratio $\varepsilon 1$ at the boundary B1 between the front mass 33 and elements unit 31 can further be decreased.

As described above, in the present embodiment, even when the resonance frequency Fr has varied in accordance with the physicality of the connected probe 8, the variance of the first transformation ratio $\varepsilon 1$ at the boundary B1 between the front mass 33 and elements unit 31 and the variance of the second transformation ratio $\varepsilon 2$ at the boundary B2 between the back mass 32 and elements unit 31 become smaller. Since the variance of the first transformation ratio $\varepsilon 1$ and the variance of the second transformation ratio $\varepsilon 2$ become smaller, the variance of the amplitude of the longitudinal vibration in the probe 8 (i.e. the part located on the distal direction side with respect to the front mass 33A) becomes smaller. Thereby, even when the resonance frequency Fr has varied in accordance with the physicality of the connected probe 8, the variance of the amplitude of the longitudinal vibration in the treatment section 17 of the probe 8 can be reduced, and the stable treatment performance can be ensured.

(Modifications)

Figure 10:
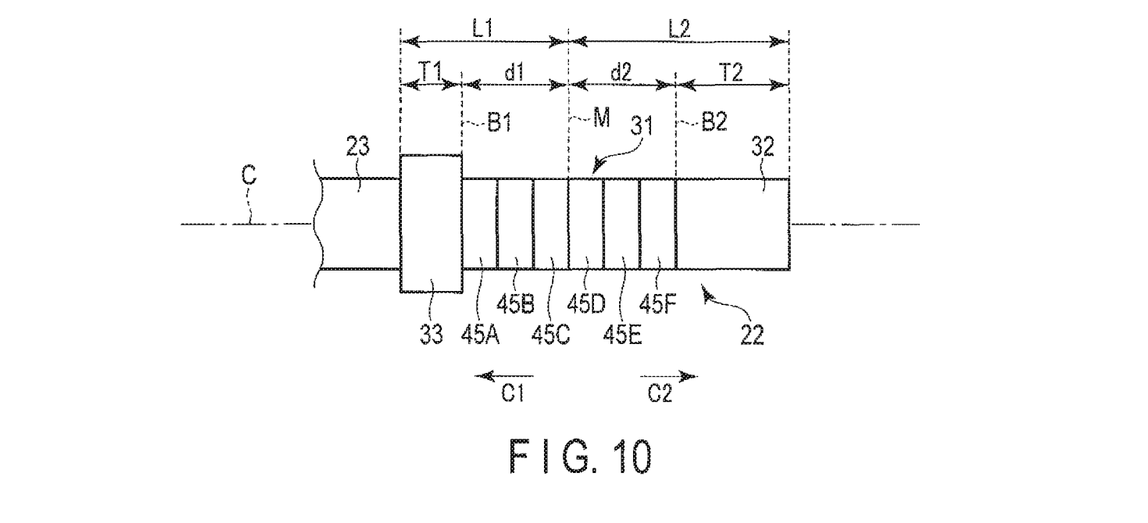
FIG. 10 is a schematic view illustrating the configuration of a vibration generating unit according to a first modification.

In the meantime, in the first embodiment, the acoustic impedance $Z1$ of the front mass 33 is made greater than the acoustic impedance $Z2$ of the back mass 32, by making the acoustic characteristic impedance ζ (at least either the propagation velocity c of sound or the density ρ), which is the physicality value, greater in the front mass 33 than in the back mass 32. However, the restriction to this is unnecessary. For example, as illustrated in FIG. 10 as a first modification, the cross-sectional area S1 of the front mass 33 perpendicular to the transmitting direction of the ultrasonic vibration (longitudinal axis C) may be made greater than the cross-sectional area S2 of the back mass 32 perpendicular to the transmitting direction of the ultrasonic vibration. In the present modification, in the front mass 33 and back mass 32, the material for forming them is identical and the acoustic characteristic impedance ζ (the propagation velocity c of sound and the density ρ) is identical. As indicated by equation (2) of the first embodiment, the acoustic impedance $Z$ varies in accordance with the cross-sectional area S perpendicular to the transmitting direction of the ultrasonic vibration, in addition to the acoustic characteristic impedance ζ. Accordingly, in the present modification, too, the acoustic impedance $Z$ becomes greater in the front mass 33 than in the back mass 32. Incidentally, the cross-sectional area S0 perpendicular to the longitudinal axis C of the elements unit 31 is identical to the cross-sectional area S2 of the back mass 32. Thus, in the front mass 33, the cross-sectional area S perpendicular to the transmitting direction of the ultrasonic vibration is increased relative to the elements unit 31.

In addition, in the present modification, too, the dimension T1 of the front mass 33 in the longitudinal direction is less than the dimension T2 of the back mass 32 in the longitudinal direction. Accordingly, in this modification, too, the dimension (first attachment dimension) L1 from the elements central position M of the elements unit 31 to the distal end of the front mass 33 is less than the dimension (second attachment dimension) L2 from the elements central position M to the proximal end of the back mass 32. In addition, in this modification, too, since the acoustic impedance Z becomes greater in the front mass 33 than in the back mass 32, the above-described functions and advantageous effects of the first embodiment can be obtained. Specifically, even when the resonance frequency Fr has varied in accordance with the physicality of the connected probe 8, the variance of the first transformation ratio ε1 at the boundary B1 between the front mass 33 and elements unit 31 and the variance of the second transformation ratio ε2 at the boundary B2 between the back mass 32 and elements unit 31 become smaller.

Figure 11:
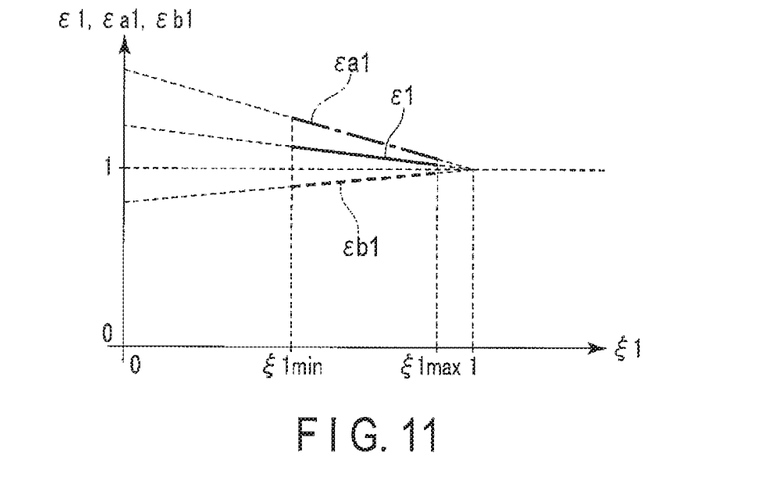
FIG. 11 is a schematic view illustrating a relation of a first transformation ratio, a transformation component of physicality and a transformation component of cross-section relative to a first distance rate in the first modification.

Here, like the first embodiment, the first distance rate ξ1 and first transformation ratio ε1 of amplitude are defined. In addition, an index value, which is indicative of the influence of the variation of physicality (acoustic characteristic impedance ζ) of material at the boundary B1 (the distal end of the elements unit 31) between the front mass 33 and elements unit 31 upon the amplitude, is set as a transformation component of physicality εa1. An index value, which is indicative of the influence of the variation of the cross-sectional area S at the boundary B1 between the front mass 33 and elements unit 31 upon the amplitude, is set as a transformation component of cross-section εb1. The first transformation ratio ε1 is determined based on the transformation component of physicality εa1 and transformation component of cross-section εb1. FIG. 11 is a view illustrating a relation of the first transformation ratio ε1, transformation component of physicality εa1 and transformation component of cross-section εb1 relative to the first distance rate ξ1 in the first modification. In FIG. 11, the abscissa indicates the first distance rate ξ1, and the ordinate indicates the first transformation ratio ε1, transformation component of physicality εa1 and transformation component of cross-section εb1. In addition, in FIG. 11, the variation of first transformation ratio ε1 is indicated by a solid line, the variation of transformation component of physicality εa1 is indicated by a dot-and-dash line, and the variation of transformation component of cross-section εb1 is indicated by a broken line.

As illustrated in FIG. 11, as the first distance rate ξ1 increases, the node position (reference node position) N1 shifts away from the boundary B1 between the front mass 33 and elements unit 31, and the first transformation ratio ε1, transformation component of physicality εa1 and transformation component of cross-section εb1 become closer to 1. Here, since the acoustic characteristic impedance ζ becomes smaller in the front mass 33 than in the elements unit 31, the acoustic characteristic impedance ζ (physicality of material) varies at the boundary B1 in such a state as to increase the amplitude of the longitudinal vibration. Accordingly, the transformation component of physicality εa1 has a value greater than 1. Thus, as the first distance rate ξ1 increases, the transformation component of physicality εa1 becomes smaller. On the other hand, since the cross-sectional area S of the front mass 33 becomes greater than that of the elements unit 31, the cross-sectional area S varies at the boundary B1 in such a state as to decrease the amplitude of the longitudinal vibration. Accordingly, the transformation component of cross-section εb1 has a value smaller than 1. Thus, as the first distance rate ξ1 increases, the transformation component of cross-section εb1 becomes greater.

In the present modification, at the boundary B1, the influence upon amplitude of the transformation component of physicality εa1 becomes greater than the influence upon amplitude of the transformation component of cross-section εb1. Accordingly, at the boundary B1, the amplitude of longitudinal vibration is increased, and the first transformation ratio ε1 becomes greater than 1. Thus, as the first distance rate ξ1 increases, the first transformation ratio ε1 becomes smaller.

Here, like the first embodiment, the variation amount ratio α, which is the ratio of the variation amount of the first transformation ratio ε1 relative to the variation amount of the first distance rate ξ1, is defined. The variation amount ratio α is indicative of an absolute value of an inclination in the variation of the first transformation ratio ε1 in FIG. 11. In this modification, the acoustic characteristic impedance ζ becomes smaller in the front mass 33 than in the elements unit 31, whereas the cross-sectional area S becomes greater in the front mass 33 than in the elements unit 31. Thus, at the boundary B1, the transformation component of physicality ξa1, which decreases as the first distance rate ξ1 increases, and the transformation component of cross-section εb1, which increases as the first distance rate ξ1 increases, influence the variation of the amplitude. Specifically, the first transformation ratio ε1 suffers the influences of the transformation component of physicality Eat and transformation component of cross-section εb1, which have mutually opposite variation characteristics in FIG. 11. Accordingly, in the present modification, the variation amount ratio α of the variation amount of the first transformation ratio ε1 relative to the variation amount of the first distance rate ξ1 becomes smaller.

As described above, in the present modification, by making the acoustic impedance Z (cross-sectional area S) greater in the front mass 33 than in the back mass 32, the variation amount ratio α of the variation amount of the first transformation ratio ε1 relative to the variation amount of the first distance rate ξ1 becomes smaller. Accordingly, even if the resonance frequency Fr varies in accordance with the probe 8 that is connected, it is possible to decrease the variation of the first transformation ratio ε1 at the boundary B1 between the front mass 33 and elements unit 31.

Figure 12:
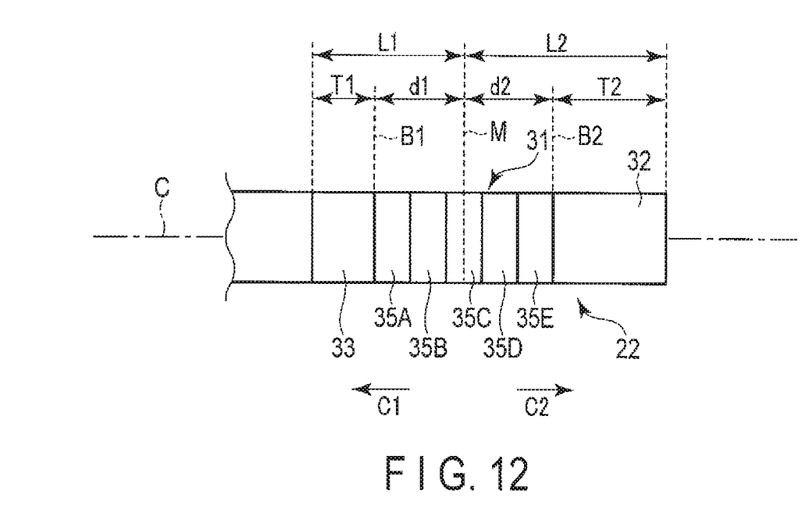
FIG. 12 is a schematic view illustrating the configuration of a vibration generating unit according to a second modification.

Besides, in the first embodiment, although six (even number) piezoelectric elements 35A to 35F are provided in the elements unit 31, five (odd number) piezoelectric elements 35A to 35E may be provided in the elements unit 31, as illustrated in FIG. 12 as a second modification. In the present modification, the elements central position M, which is the central position of the elements unit 31 in the longitudinal direction, agrees with the central position in the thickness direction of the piezoelectric element 35C. In this modification, the piezoelectric elements 35A and 35B are located on the distal direction side with respect to the elements central position M, and the piezoelectric elements 35D and 35E are located on the proximal direction side with respect to the elements central position M.

In the present modification, too, the acoustic characteristic impedance ζ0 of material is greater in the front mass 33 than in the back mass 32, and the acoustic impedance Z is greater in the front mass 33 than in the back mass 32. In addition, also in this modification, the dimension T1 of the front mass 33 in the longitudinal direction is less than the dimension T2 of the back mass 32 in the longitudinal direction. Accordingly, in this modification, too, the dimension (first attachment dimension) L1 from the elements central position M of the elements unit 31 to the distal end of the front mass 33 is less than the dimension (second attachment dimension) L2 from the elements central position M to the proximal end of the back mass 32.

Additionally, by combining the first embodiment and the first modification, the acoustic characteristic impedance ζ of material may be made greater in the front mass 33 than in the back mass 32, and the cross-sectional area S perpendicular to the transmitting direction of the ultrasonic vibration may be made greater in the front mass 33 than in the back mass 32. In this case, too, from the above-described equation (2) of the first embodiment, the acoustic impedance Z becomes greater in the front mass 33 than in the back mass 32.

Additionally, in the ultrasonic treatment instrument 2, while the ultrasonic vibration is transmitted to the treatment section 17 of the probe 8, high-frequency electric power (high-frequency electric energy) may be supplied from the energy source unit 10 to the treatment section 17 and jaw 7, and the treatment section 17 and jaw 7 may be configured to function as electrodes of the high-frequency electric power. By the treatment section 17 and jaw 7 functioning as the electrodes, a high-frequency current flows in the treated target that is grasped between the jaw 7 and treatment section 17, the treated target is denatured, and coagulation is promoted. In this case, although the high-frequency electric power is supplied to the treatment section 17 through the rod-shaped member 23 and probe 8, electrical insulation is effected between the rod-shaped member 23 and the piezoelectric elements (35A to 35F) and the high-frequency electric power, which is supplied to the treatment section 17, is not supplied to the piezoelectric elements (35A to 35F). However, in this case, too, an electric current (AC current), which causes an ultrasonic vibration, is supplied to the piezoelectric elements (35A to 35F).

Additionally, the jaw 7 may not be provided on the ultrasonic treatment instrument 2. In this case, for example, the treatment section 17, which projects from the distal end of the sheath 6, is formed in a hook shape. In the state in which the treated target is caught on the hook, the treatment section 17 is vibrated by an ultrasonic vibration and the treated target is resected.

In the above-described embodiment, etc. (excluding the comparative example), the vibration generating unit (22) includes the element unit (31). The element unit (31) includes the piezoelectric element (35A to 35F; 35A to 35E) which is configured to generate an ultrasonic vibration by being supplied with electric power. The proximal-side fixing member (32) abuts on the element unit (31) from the proximal direction side, and the distal-side fixing member (33) abuts on the element unit (31) from the distal direction side. The element unit (31) is sandwiched between the proximal-side fixing member (32) and the distal-side fixing member (33) in the longitudinal direction. The ultrasonic vibration, which is generated in the element unit (31), is transmitted toward the distal direction side through the distal-side fixing member (33). The acoustic impedance (Z) is greater in the distal-side fixing member (33) than in the proximal-side fixing member (32).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A vibration generating unit vibrating in a predetermined frequency range, the vibration generating unit comprising:
an element unit including a piezoelectric element which is configured to generate an ultrasonic vibration by being supplied with electric power, the element unit having a proximal end and a distal end, and extending along a longitudinal axis from the proximal end to the distal end;
a proximal-side fixing member made of metal and abutting on the element unit from a proximal direction side;
a distal-side fixing member made of metal and abutting on the element unit from a distal direction side, the distal-side fixing member being configured such that the element unit is sandwiched between the proximal-side fixing member and the distal-side fixing member in a longitudinal direction which is parallel to the longitudinal axis, and being configured to transmit the ultrasonic vibration, which is generated in the element unit, toward the distal direction side, the distal-side fixing member having a greater acoustic impedance than the proximal-side fixing member; and
a vibration transmitting member which is a separate body from the element unit, the proximal-side fixing member, and the distal-side fixing member, and which abuts on a distal end of the distal-side fixing member, the vibration transmitting member extending from the distal end of the distal-side fixing member toward the distal direction side along the longitudinal axis, the vibration transmitting member being configured to be connected to a probe from the proximal direction side in a region located on the distal direction side with respect to the distal-side fixing member, the vibration transmitting member being configured to transmit the ultrasonic vibration, which is transmitted from the element unit through the distal-side fixing member, to the probe, thereby transmitting the ultrasonic vibration toward a treatment section in a distal portion of the probe;
wherein:
the piezoelectric element has a greater acoustic impedance than each of the proximal-side fixing member and the distal-side fixing member;
an antinode is in alignment with the proximal end of the proximal-side fixing member;
the proximal-side fixing member is made of extra super duralumin;
the distal-side fixing member is made of 64 titanium alloy, stainless steel or lead zirconate titanate; and
a dimension between the distal end of the distal-side fixing member and a connecting position of the vibration transmitting member to the probe in the longitudinal direction is larger than each of a dimension of the proximal side fixing member in the longitudinal direction and a dimension of the element unit in the longitudinal direction.

2. A vibration generating unit vibrating in a predetermined frequency range, the vibration generating unit comprising:
an element unit including a piezoelectric element which is configured to generate an ultrasonic vibration by being supplied with electric power, the element unit having a proximal end and a distal end, and extending along a longitudinal axis from the proximal end to the distal end;

a proximal-side fixing member made of metal and abutting on the element unit from a proximal direction side;

a distal-side fixing member made of metal and abutting on the element unit from a distal direction side, the distal-side fixing member being configured such that the element unit is sandwiched between the proximal-side fixing member and the distal-side fixing member in a longitudinal direction which is parallel to the longitudinal axis, and being configured to transmit the ultrasonic vibration, which is generated in the element unit, toward the distal direction side, the distal-side fixing member having a greater acoustic impedance than the proximal-side fixing member; and a vibration transmitting member which is a separate body from the element unit, the proximal-side fixing member, and the distal-side fixing member, and which abuts on a distal end of the distal-side fixing member, the vibration transmitting member extending from the distal end of the distal-side fixing member toward the distal direction side along the longitudinal axis, the vibration transmitting member being configured to be connected to a probe from the proximal direction side in a region located on the distal direction side with respect to the distal-side fixing member, the vibration transmitting member being configured to transmit the ultrasonic vibration, which is transmitted from the element unit through the distal-side fixing member, to the probe, thereby transmitting the ultrasonic vibration toward a treatment section in a distal portion of the probe;

wherein:

the piezoelectric element has a greater acoustic impedance than each of the proximal-side fixing member and the distal-side fixing member;

a dimension of the distal-side fixing member in the longitudinal direction is less than a dimension of the proximal-side fixing member in the longitudinal direction;

the proximal-side fixing member is made of extra super duralumin;

the distal-side fixing member is made of 64 titanium alloy, stainless steel or lead zirconate titanate; and a dimension between the distal end of the distal-side fixing member and a connecting position of the vibration transmitting member to the probe in the longitudinal direction is larger than each of a dimension of the proximal side fixing member in the longitudinal direction and a dimension of the element unit in the longitudinal direction.

3. The vibration generating unit of claim 2, wherein the piezoelectric element is configured to generate the ultrasonic vibration, thereby vibrating the element unit, the proximal-side fixing member, and the distal-side fixing member in a predetermined frequency range in which one of node positions is located in the element unit.

4. The vibration generating unit of claim 3, wherein in a state in which the element unit, the proximal-side fixing member, and the distal-side fixing member vibrate in the predetermined frequency range, a first length corresponding to a ¼ wavelength of a vibration from a reference node position, which is a node position located in the element unit, toward the distal direction side is smaller than a second length corresponding to a ¼ wavelength of the vibration from the reference node position toward the proximal direction side.

5. The vibration generating unit of claim 4, wherein in a state in which the element unit, the proximal-side fixing member, and the distal-side fixing member vibrate at a predetermined resonance frequency included in the predetermined frequency range, a dimension between the reference node position and the distal end of the distal-side fixing member in the longitudinal direction has a length equal to the first length, and a dimension between the reference node position and a proximal end of the proximal-side fixing member in the longitudinal direction has a length equal to the second length.

6. The vibration generating unit of claim 5, wherein in a state in which the element unit, the proximal-side fixing member, and the distal-side fixing member vibrate in the predetermined frequency range, a most proximal antinode position, which is located most proximally among antinode positions of vibration, is located at the proximal end of the proximal-side fixing member.

7. The vibration generating unit of claim 3, wherein, when a central position between the distal end and the proximal end of the element unit in the longitudinal direction is set as an element central position, the piezoelectric element is symmetrically arranged with respect to the element central position in the longitudinal direction.

8. The vibration generating unit of claim 7, wherein in a state in which the element unit, the proximal-side fixing member, and the distal-side fixing member vibrate at a predetermined resonance frequency included in the predetermined frequency range, a reference node position, which is a node position located in the element unit, agrees with the element central position.

9. The vibration generating unit of claim 2, wherein at least either a density or a propagation velocity of sound is greater in the distal-side fixing member than in the proximal-side fixing member.

10. The vibration generating unit of claim 2, wherein the distal-side fixing member has a greater cross-sectional area perpendicular to the longitudinal axis than the proximal-side fixing member.

11. A vibrating body unit comprising:
the vibration generating unit of claim 2; and
the probe connected to the vibration transmitting member of the vibration generating unit.

12. An ultrasonic treatment instrument comprising:
the vibrating body unit of claim 11; and
a holding unit configured such that the probe extends from an inside of the holding unit toward the distal direction side.

13. An ultrasonic treatment instrument comprising:
The vibration generating unit of claim 2; and
the probe to which the vibration transmitting member is connected from the proximal direction side.

* * * * *